United States Patent [19]

Batenhorst et al.

[11] Patent Number: 5,466,700
[45] Date of Patent: Nov. 14, 1995

[54] ANESTHETIC USE OF N-PHENYL-N-(4-PIPERIDINYL)AMIDES

[75] Inventors: Randal L. Batenhorst; Anthony W. Fox, both of Raleigh, N.C.

[73] Assignee: Glaxo Wellcome Inc., Research Triangle Park, N.C.

[21] Appl. No.: 114,032

[22] Filed: Aug. 30, 1993

[51] Int. Cl.$^6$ .................... A61K 31/445; A61K 31/55; A61K 31/08

[52] U.S. Cl. .................... 514/329; 514/327; 514/220; 514/722

[58] Field of Search ....................... 514/327, 329

[56] References Cited

U.S. PATENT DOCUMENTS 5,019,583  5/1991  Feldman et al. ................. 514/327

*Primary Examiner*—Jerome D. Goldberg
*Attorney, Agent, or Firm*—R. Cole Harrington

[57] ABSTRACT

The use of particular opioids to induce and maintain anesthesia and conscious sedation is disclosed. The opioids used in the method of the present invention relate to the anesthetic action of the N-phenyl-N-(4-piperidinyl)amides as disclosed in U.S. Pat. No. 5,019,583 to Feldman, et al.

27 Claims, No Drawings

ANESTHETIC USE OF N-PHENYL-N-(4-PIPERIDINYL)AMIDES

DESCRIPTION

1. Field of Invention

The present invention relates to the use of particular opioids to induce and maintain anesthesia. More particularly, the present invention relates to the anesthetic action of the N-phenyl-N-(4-piperidinyl)amides disclosed in U.S. Pat. No. 5,019,583 to Feldman, et al.

2. Background of the Invention

One of the well accepted techniques for inducing an effective general anesthesia state is to administer to the patient a combination of drugs which provides a balanced combination of loss of consciousness or hypnosis, analgesia, and muscle relaxation. Typically, patients receive a low dose of an opioid to provide analgesia and a hypnotic and/or anxiolytic drug as a primary anesthetic to render them unconscious. Once unconscious, the patient's anesthesia state is maintained on a combination of drugs, such as a hypnotic or a potent inhaled agent like isoflurane or enflurane, with intermittent doses of an opioid at analgesic levels to provide additional analgesia at times of surgical stress.

Generally, the time it takes a patient to recover from the effects of an anesthesia regimen is variable and is dependent upon the duration and magnitude of the exposure to the opioid as well as the primary anesthetic. Due to the long duration of action of conventional opioids currently used in anesthesia protocols, these opioids are typically administered in "low doses" at levels no higher than necessary to render effective analgesia to the patient. As previously mentioned, hypnotic and/or anxiolytic drugs are employed as primary anesthetics and administered in conjuction with the opioid to render the patient unconscious.

Despite the practice of employing hypnotics and/or anxiolytics as the primary anesthetic, it is known that certain conventional opioids can be administered at dose levels up to 10 times higher than their effective analgesic doses in order to induce and maintain anesthesia. At such dosage levels, the opioid is considered a primary anesthetic since it induces and maintains unconsciousness as well as providing analgesia. Furthermore, at these elevated dose levels, the opioids are capable of markedly reducing the dosing requirements of any accompanying hypnotics, anxiolytics and/or inhaled agents by 50 to 80%. Unfortunately, currently available opioids are not generally used as primary anesthetics due to their long duration of action and the undesireable effects associated with elevated dose levels.

In particular, continued administration of such conventional opioids at elevated doses throughout the surgical procedure leads to marked delays in recovery of mental and respiratory function. Since the time to patient recovery is variable and dependent upon the duration and magnitude of the exposure to the opioid, recovery times become longer and longer with prolonged exposures to higher doses.

For example, the time for the concentration of such an opioid in the blood to fall from an anesthetic concentration (a high dosage) to an analgesic concentration (a low dosage), and subsequently to a level that allows for full recovery, increases with the size and duration of the dose so that the delay in recovery places the patient at risk for recurrent respiratory depression or an unexpected cessation in breathing.

Additionally, conventional opioids would be poor candidates for a primary anesthetic as they lack the necessary response time required by the physician for rapidly decreasing or increasing the level of anesthesia in accordance with changing surgical stimuli. For example, morphine is an opioid which is effective as an analgesic but is not useful as an anesthetic because it has a slow onset of action, causes hypotension due to the release of histamine and has a prolonged effect when given at high doses.

Consequently, the use of conventional opioids at anesthetic or high doses has typically been avoided by the medical community to date due to the problems with response time and prolonged patient recovery time associated with these drugs. Indeed, the general practice in conventional opioid anesthesia is to maintain the patient on the lowest amount of opioid possible while still providing an effective dosage for inducing and maintaining analgesia. Such an approach minimizes the patient's recovery time with respect to the opioid but requires that the opioid be combined with an appreciable dose of a hypnotic or anxiolytic drug, as mentioned above, in order to provide an adequate anesthetic regimen. Unfortunately, such dosage levels of these additional drugs tends to lengthen recovery times. Even in cases where these additional drugs are administered at minimal doses, undesireably long patient recovery times are still unavoidable due to the presence of analgesic levels of conventional opioids which, as discussed above, require an appreciable length of time to be metabolized.

In light of the rapidly growing trends toward outpatient surgery and the desire to extubate inpatients in a timely fashion, a need has been identified for new methods of providing short-acting anesthesia and, in particular, for methods which minimize or avoid the use of longer acting drugs. It would therefore be desireable to provide a new method of optimizing the induction and maintenance of anesthesia in mammals wherein the level of anesthesia can be readily adjusted and the adverse events associated with patient recovery are minimized.

SUMMARY OF THE INVENTION

The present invention is a new method for the induction and maintenance of anesthesia as well as conscious sedation using N-phenyl-N-( 4-piperidinyl)amides as disclosed in U.S. Pat. No. 5,019,583 to Feldman, et al., which is incorporated herein by reference thereto.

U.S. Pat. No. 5,019,583 to Feldman, et al. discloses a specific class of N-phenyl-N-(4-piperidinyl)amides and, particularly, methyl[4-(methoxycarbonyl)-4-[(1-oxopropyl)phenylamino]-1-piperidine]-propanoate, monohydrochloride (now known as remifentanil), which are -opioids. These amides are potent analgesics characterized by rapid onset and an exceptionally short terminal half-life. The short half-life of such amides has been attributed to their rapid enzymatic metabolism in the blood as contrasted with the slower metabolism of other opioids in the liver. The ester linkage in the pendant chain from the piperidine nitrogen renders the amides susceptible to inactivation by plasma and tissue esterases.

It has now been found that the N-phenyl-N-(4-piperidinyl)amides disclosed the Feldman, et al. patent, and particularly remifentanil, are ideal for anesthetic use in the induction and maintenance of anesthesia as well as conscious sedation and are particularly useful in variable rate infusion due to their short terminal half-life and distribution characteristics. Unlike conventional opioids, the amides used in the method of the present invention can be administered as primary anesthetics at dosage levels in excess of that required for inducing and maintaing analgesia without many of the undesireable side effects which would be predicted at such opioid dosages. These amides exhibit hemodynamic stability similar to other N-phenyl-N-( 4-piperidinyl)amides, but unlike other N-phenyl-N(4-piperidinyl)amides, these amides, and particularly remifentanil, have very rapid onset of action and an extremely short duration of action. These characteristics allow the physician to titrate the rate of administration of the amides to match the patient's surgical stimulus without fear of prolonged respiratory depression at the end of the procedure.

For example, it has been shown in man that changes in remifentanil's concentration in the blood are reflective of changes in the brain's electroencephalographic activity and are out of synchronism by only 1 to 2 minutes. Thus, rapid changes in blood concentration are reflected as rapid changes in anesthetic activity.

Moreover, since the opioids used in the method of the present invention can be administered in relatively high dosages as a primary anesthetic, the dosage level of any accompanying drugs, such as hypnotics and/or an anxiolytics which require appreciable time to be metabolized, may be reduced. As a result, patient recovery times are reduced relative to other anesthesia protocols where dosage levels of conventional opioids are limited to analgesic levels and hypnotic and/or anxiolytic drugs are employed at higher dosage levels to serve as the primary anesthetic. Alternatively, these opioids may be used to provide conscious sedation in a patient for procedures where it is desirable avoid levels of unconsciousness associated with a complete anesthesia regimen. The rapid onset of action and extremely short duration of action are similarly advantageous in this setting as well.

In accordance with the present invention, the compounds of Formula (I), as set forth in U.S. Pat. No. 5,019,583 to Feldman, et al., are administered to provide the primary anesthetic function in a patient. Typically, the amides are used in combination with a minimal dosage of a hypnotic, an anxiolytic or a central nervous system depressant as part of a balanced anesthesia regimen to render the patient unconscious. Alternatively, the amides used in the method of the present invention may also be used to induce or maintain conscious sedation or light anesthesia in a patient, such as an adjunct to a spinal or local anesthetic for example. The amides are also useful in anesthetic protocols for surgeries such as certain cardiovascular surgeries where avoiding cardiac depressant anesthetics is desirable.

DETAILED DESCRIPTION OF THE INVENTION

The present invention is a method for providing anesthesia or conscious sedation in a mammal which comprises administering to such mammal a therapeutically effective amount of a compound having the Formula (I) as set forth below:

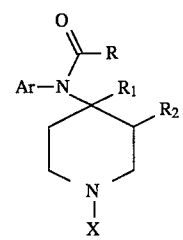

wherein X is a member selected from the group consisting of alkoxycarbonyl-lower alkyl, lower alkylcarbonyloxy-lower alkyl, alkenyloxycarbonyl-lower alkyl, and $(C_{1-2})$alkoxy-$(C_{1-2})$alkoxycarbonyl-lower alkyl; Ar is a member selected from the group consisting of phenyl (preferred) and mono-,di- and tri-substituted phenyl, particularly mono-substituted in the 2-position, wherein each substituent is independently selected from the group consisting of halo, lower alkyl, lower alkoxy and trifluoromethyl; R is a member selected from the group consisting of lower alkyl, particularly ethyl, and lower alkoxy-lower alkyl, particularly methoxymethyl; $R^1$ is a member selected from the group consisting of hydrogen, lower alkoxycarbonyl, particularly methoxycarbonyl, and methoxymethyl; and $R^2$ is a member selected from the group consisting of hydrogen and methyl. Moreover, the method of the present invention may employ the optically active and cis-trans isomers of the aforementioned compounds as well as the acid addition salts, particularly the pharmaceutically acceptable acid addition salts of said compounds and isomers. The compounds are administered in an anesthetic amount in excess of that which would merely induce or maintain analgesia.

As used in the foregoing definitions the term "lower" is meant to modify the so-indicated group by indicating from 1 to 4 carbon atoms; the terms "alkyl", "alkoxy" and "alkenyl" are each meant to respectively include straight and branch chained hydrocarbons, e.g. of about 1 to 10 carbons and include the group of hydrocarbons having 1 to 4 carbons; and the term "halo" is generic to halogens of atomic weight less than 127, i.e., fluoro, chloro, bromo and iodo.

In particular, the method of the present invention employs compounds disclosed in the U.S. Pat. No. 5,019,583 and, more particularly, the compounds set forth below.

1. 3-[4-[(1-Oxopropyl)phenylamino]-1-piperidine]propanoic acid methyl ester
2. 4-[4-[(1-Oxopropyl)phenylamino]-1-piperidine]butanoic acid, methyl ester
3. 3-[4-[(1-Oxopropyl)phenylamino]-1-piperidine]propanoic acid, methoxymethyl ester
4. 2-[4-[(1-Oxopropy)phenylamino]-1-piperidine]ethyl acetate
5. 3-[4-Methoxycarbonyl-4-[(1-oxopropyl)phenylamino]-1-piperidine]propanoic acid, methyl ester (remifentanil)
6. 3-[4-Methoxycarbonyl-4-[(1-oxopropyl)phenylamino]-1-piperidine]pentanoic acid, methyl ester
7. 3-[4-Methoxycarbonyl-4-[(1-oxopropyl)phenylamino]-1- piperidine]propanoic acid, methoxymethyl ester
8. 3-[4-Methoxycarbonyl-4-[(1-oxopropyl)phenylamino]-1-piperidine]propanoic acid, vinyl ester
9. 3-[4-Methoxycarbonyl-4-[(1-oxopropyl)phenylamino]-1-piperidine] -ethyl acetate
10. 3-[4-[(1-Oxopropyl)-2-fluorophenylamino]-1- piperidine] propanoic acid, methyl ester
11. 3-[4-(1-Oxopropyl)-2-fluorophenylamino]-1-piperidine]propanoic acid, vinyl ester
12. 3-[4-[(1-Oxopropyl)-2-fluorophenylamino]-1-piperidine]propanoic acid, 3-butenyl ester
13. 3-[4-[(2-Methoxy-1-oxoethyl)phenylamino]-1-piperidine] propanoic acid, methyl ester
14. 3-[4-[(2-Methoxy-1-oxoethyl)fluorophenylamino]-1-piperidine]propanoic acid, methyl ester
15. [+]-Cis-3-[3-methyl-4-(1-oxopropyl)phenylamino]-1-piperidine]propanoic acid, methyl ester
16. [+]-Cis-3-[3-methyl-4-(1-oxopropyl)phenylamino]-1-piperidine]propanoic acid, methoxymethyl ester
17. [+]-Cis-3-[3-methyl-4-(1-oxopropyl) phenylamino]-1-piperidine]propanoic acid, allyl ester
18. [+]-Cis-3-[3-methyl-4-( 1 -oxopropyl)phenylamino]-1-piperidine] propanoic acid, allyl ester
19. [+]-Cis-2-[3-methyl-4-(1-oxopropyl)phenylamino]-1-piperidine]ethyl acetate
20. [−]-Cis-3-3R-methyl-4S-(1-oxopropyl)phenylamino]-1-piperidine]propanoic acid, methyl ester
21. Trans-3-[3-methyl-4-[(1-oxopropyl)phenylamino]-piperidine]propanoic acid, methyl ester
22. [+]-Cis-3-[3-methyl-4-(1-oxopropyl)-2-fluorophenylamino]-1-piperidine]propionic acid, methyl ester
23. [+]-Cis-3-[3-methyl-4-(1-oxopropyl)-2-fluorophenylamino]-1-piperidine]propanoic acid, allyl ester Various synthetic routes for preparing the compounds used in the method of the present invention are set forth in U.S. Pat. No. 5,019,583 which, as previously mentioned, is incorporated herein by reference thereto.

The method of the present invention includes the use of pharmaceutically-acceptable salts and isomers of those compounds. For example, the compounds of Formula (I) may be converted to the therapeutically active acid addition salt form by treatment with an appropriate acid as discussed in the Feldman et al. patent. Alternatively, the salt form of these compounds can be converted by treatment with alkali to the free base form. In addition, the salt forms may be useful in the preparation of other salt forms, for example, as intermediates for conversion into the preferred pharmaceutically acceptable salt derivatives. Furthermore, the particular salt may exist as a solvate, e.g., a hydrate or a hemihydrate.

Several of the compounds of Formula (I) have one or more asymmetric carbon atoms in their structure and consequently they may exist in the form of different optical isomeric forms or mixtures, e.g., racemates, of such forms. For example, when $R^2$ in Formula (I) represents a methyl group, there are two asymmetric carbon atoms in the piperidine ring.

As set forth in the '583 patent to Feldman, et al., enantiomeric forms and mixtures of such forms may be obtained separately by the application of methods of resolution known to those skilled in the art such as salt formation with an optically active acid followed by selective crystallization or chiral derivatization, in turn, followed by selective crystallization or silica gel chromatography.

Amides of Formula (I) having the cis- or trans-configuration, essentially free of one another, may be obtained, for example, by initiating their preparation from pure cis- or trans-isomers of the appropriate precursors. Alternatively, substantially pure forms of the cis- and transisomer compounds of Formula (I) may be obtained, substantially free of the other isomer, by separating a mixture of such appropriate precursor forms by silica gel chromatography. Cis- and trans-forms may in turn be further resolved into their optical enantiomers, such that they are essentially free of their optical counterpart, by the application of methodologies known in the art such as the aforementioned techniques. All racemic and isomeric forms of the amides of Formula (I), including diastereomeric mixtures, pure diastereomers and enantiomers, and mixtures thereof, are intended to be within the scope of this invention.

The compounds used in the method of the present invention are generally administered in an amount in excess of an amount effective for analgesia (e.g., an amount in excess of its $ED_{50}$ for analgesia) in conjunction with a hypnotic such as propofol (commercially available from Stuart Pharmaceuticals under the name DIPRIVAN®) or an anxiolytic, such as a benzodiazepine like midazolam (commercially available from Roche Laboratories under the tradename VERSED® or an inhaled agent such as isoflurane), as part of a balanced or total intravenous anesthesia technique preferably in an amount less than 50% of their respective $ED_{50}$. The hypnotic or anxiolytic is typically administered preoperatively to provide mild sedation while the amide is administered at anesthetic doses by single injection or by continuous infusion to render the patient unconscious. These amides, and particularly remifentanil, may also be used with nitrous oxide and other inhaled agents, such as isoflurane. Alternatively, these amides may be administered in conjunction with a CNS depressant to induce unconsciousness.

The amount of the amides to be administered to induce anesthesia or conscious sedation will vary depending upon the specific compound administered, the condition of the patient, the patient's response to stress events, the other drugs with which the compound is administered and the nature and depth of the anesthesia desired. Although the dosage will vary in accordance with the invention, the compounds are administered to the patient in an amount in excess of the amount in which they would otherwise be effective for analgesia given the condition of the mammal or patient (one factor contributing to the condition of the patient being the other drugs administered in conjunction with the amide in the anesthetic treatment, for example).

Generally, the compounds are intravenously administered in an amount in excess of their $ED_{50}$ for analgesia, and typically in an amount about 4 to 10 times their $ED_{50}$ for analgesia. ($ED_{50}$ is defined herein as the dose of a drug which produces a pre-determined quantal response in 50% of test subjects). For example, remifentanil has an $ED_{50}$ for analgesia of about a 1 g/kg bolus or about 0.05 to about 0.1 g/kg/min by continuous infusion. For inducing anesthesia, as indicated by loss of consciousness or maximal slowing of the EEG, the $ED_{50}$ for remifentanil is about a 10 g/kg bolus or about 1 g/kg/min by continuous infusion. Dosage amounts for conscious sedation will vary as explained above but can be readily calculated by one skilled in the art from the ranges provided herein for anesthesia.

When administered parenterally in a single dose to induce anesthesia, a suitable dosage amount for the compounds of the present invention is from about 8 to about 20 g/kg and, more particularly, from about 3 to about 10 g/kg. Results from an ongoing study in 85 patients (70 patients completed) demonstrated that single intravenous doses of remifentanil with no other medications rendered approximately 70% of the patients unconscious. When the amides are administered by continuous infusion to induce anesthesia, suitable rates for administration are from about 1 to about 8 g/kg/min and, more particularly, from about 1 to about 2 g/kg/min. A normal volunteer study examining the electroencephalographic effects of remifentanil administered by continuous infusion at rates of 1 to 8 g/kg/min provided evidence that 100% of the volunteers were rendered unconscious within 3–5 minutes as evidenced by delta wave formation on the EEG. When administered parenterally in conjunction with a hypnotic or an anxiolytic agent, a suitable dosage amount for the amides of the present invention is from about 2 to about 5 g/kg and the majority of all patients can be rendered unconscious.

Suitable dosage amounts for maintaining anesthesia using these compounds is provided by supplemental bolus dosages from about 1 to about 2 g/kg or by continuous infusion at rates from about 0.1 to about 3.0 g/kg/min. For example, remifentanil may be administered as a continuous infusion at rates from about 0.4 to about 2 g/kg/min in order to maintain anesthesia in conjunction with an inhaled agent (0.4–2 g/kg/min with nitrous oxide and 0.1–1 g/kg/min with isoflurane), a hypnotic (0.1–1 g/kg with propofol) or an anxiolytic. These compounds can also be delivered at suitable continuous infusion at rates from about 0.05 to about 0.2 g/kg/min as an adjunct to spinal or local anesthetics in order to sedate a patient.

In accordance with particular embodiments of the present invention, the amides are administered in an anesthetic treatment regimen which is characterized by rapid recovery of consciousness and normal respiratory function upon discontinuing administration of the amide. In particular, the mammal or patient recovers from anesthesia as indicated by return of spontaneous ventilation and response to verbal commands within about 15 minutes, and typically within about 5–10 minutes.

The amides are generally administered parenterally and, in particular, intravenously. Studies have also shown that transmembrane delivery is possible. For example, ocular absorption has been observed in rabbit studies while sublingual absorption has been observed in dogs indicating that these piperidinylamides can be administered via transmembrane delivery vehicles. Observations that the opioid, fentanyl, can be administered sublingually indicate that the amides of Formula (I) can also be similarly administered via a transoral route. These delivery modes are also effective when using the amides as an analgesic.

To prepare pharmaceutical compositions for use in this invention, an effective amount of the particular compound, in base or acid-addition salt form, as the active ingredient is combined in intimate admixture with a pharmaceutically acceptable carrier. The carrier may take a wide variety of forms depending on the form of preparation desired for administration. These pharmaceutical compositions are desirable in unitary dosage form suitable, for example, for administration orally, transdermally, intranasally, rectally, sublingually, parenterally or by inhalation. For example, in preparing the compositions in oral dosage form, any of the usual pharmaceutical media may be employed, such as water, glycols, oils, alcohols and the like. In the case of oral liquid preparations, suspensions, syrups, elixirs, solutions and the like may be employed. Solid pharmaceutical carriers such as starches, sugars, kaolin, lubricants, binders, disintegrating agents and the like may be used in the case of powders, pills, capsules and tablets.

For parenteral compositions, the carrier will usually comprise sterile water, at least in large part, although other ingredients may be added to aid solubility or to improve the delivery or stability of the composition, for example. Injectable solutions may be prepared in which the carrier comprises isotonic saline solution, glucose solution or a mixture of saline and glucose solution, for example. Injectable suspensions may also be prepared in which case appropriate liquid carriers, suspending agents and the like may be employed. Acid addition salts of the amides are more suitable in the preparation of aqueous compositions due to their increased water solubility over the corresponding base form.

In some cases it may be advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonsful and the like, and segregated multiples thereof.

The invention is illustrated in more detail by the following non-limiting examples:

EXAMPLE 1

Anesthesia was induced in male mongrel dogs (13–17 kg) with a bolus (0.3 mole/kg) (110 g/kg) of remifentanil or fentanyl depending on their assignment to either the remifentanil or fentanyl treatment groups. The dogs were intubated and anesthesia maintained with 4% or less isoflurane (Aerrane®, Anaquest, Madison, Wis.) and 40% $O_2$. Neuromuscular blockade was induced with 0.1 mg/kg pancuronium bromide (Elkins-Sinn, Cherry Hill, N.J.).

The femoral veins were cannulated for administration of test compounds. The left femoral artery was cannulated for monitoring arterial blood pressure with a pressure transducer (Micron Model MP15D, Simi Valley, Calif.). A lead II electrocardiogram was recorded from subcutaneous electrodes. A 5F or 6F pressure transducer (MIKKRO-TIP®), Millar Instruments, Houston, Tex.) was inserted through the right carotid artery into the left ventricle to monitor intraventricular pressure. The left ventricular pressure signal was differentiated (using a 100Hz low pass differential amplifier) to obtain the maximal rate of rise (+dP/dt) and used to trigger a biotachometer amplifier to record hear rate. Cardiac output was measured by thermodilution with a cardiac output (STARCOM® Model SP1465, Spectramed Inc., Oxnard, Calif.) and a 5F Swan Ganz catheter inserted into the right jugular vein and positioned in the pulmonary artery.

Six electrodes were used for recording the electroencephalogram (EEG). Two electrodes were placed in the frontoparietal areas, two in the occipital areas and two were attached to the skin of the neck as ground electrodes. Left and right hemispheric leads (occipital to frontal) were recorded. Rectal temperatures were monitored (Model 43TD Telethermometer, Yellow Springs Instrument Co. Inc., Yellow Springs, Ohio) and maintained at 37°–38° C. with a heating pad (Model TP-200, Gaymar, Orchard Park, N.Y.). Hemodynamic variables and the EEG were recorded on a Gould 3800S physiograph (Gould Inc., Cleveland, Ohio) and an $MI^2$ data acquisition system (Model Micro 5000-M100, Modular Instruments Inc., Southeastern, Pa.).

On completion of the above instrumentation, the recorded variables were allowed to stabilize for 30 min. At that time infusion of remifentanil or fentanyl was initiated. Five minutes after starting the infusion, the isoflurane was turned off and the animals were ventilated on room air for the remainder of the experiment. Supplemental doses of pancuronium were given as needed.

Remifentanil was dissolved in 0.9% NaCl and given intravenously via an infusion pump (Model 22, Harvard Instrument Co., Quincy, Mass.) except for the induction dose which was given by manual i.v. push. Doses rates ranged from 0.03 to 10 mole/kg/min in one-half log steps with 10 min at each dose rate. Cumulative doses at the end of each step were: 0.11 (induction bolus), 0.23, 0.60, 1.7, 5.5, 17 and 54 mg/kg. Fentanyl citrate (Sigma Chemical Co., St. Louis, Mo.) was also dissolved in 0.9% NaCl and administered by i.v. push or infusion pump. Dose rates for fentanyl were: 0.03, 0.1, 0.3, 1.0 and 3.0 mole/kg/min. Each dose rate was given for 10 min. resulting in cumulative doses of 0.10 (induction bolus), 0.20, 0.54, 1.5, 4.9, 15 mg/kg.

Pentylenetetrazole, a known convulsant, (Sigma Chemical Co., St. Louis, Mo.) was dissolved in 0.9% NaCl and given 5 min. after termination of the opioid infusion as a positive control. The initial dose was 1 mg/kg and was followed by additional 10 mg/kg doses until seizure activity was observed on the EEG. Seizure activity was observed in all the dogs given pentylenetetrazole at cumulative doses from 11 to 41 mg/kg. One dog did not receive pentylenetetrazole.

Data was expressed as mean ±SEM. Statistical analysis was conducted using analysis of variance as a test of overall significance and Duncan's multiple range test for pairwise comparisons (Generalized linear models procedure, SAS Statistical Analysis System, Version 6.06, SAS Institute, Cary, N.C.).

RESULTS

Electroencephalogram (EEG)

The results of the EEG study on remifentanil (denoted as GI87084) are shown in Table 1 as the mean ±SEM for 4–5 dogs. Remifentanil infused at rates from 0.03 to 10 mole/kg/min had no effects on EEG amplitude. Administration of pentylenetetrazole produced a dramatic increase (344%) in EEG amplitude.

Fentanyl produced no change in EEG amplitude at doses up to 10 mole/kg. The highest infusion rate of fentanyl produced a significant increase in baseline EEG amplitude in the right hemisphere, but no change in the left hemisphere. Seizure activity was also observed on the EEG at this dose rate. The seizures were characterized by an increase in EEG amplitude and frequency. The positive control, pentylenetetrazole, produced similar effects on the EEG.

TABLE 1

EFFECTS OF GI87084B, FENTANYL AND PENTYLENETETRAZOLE ON EEG AMPLITUDE IN ANESTHETIZED DOGS

| TIME (min) | OPIOID DOSE (μmole/kg) | EEF AMPLITUDE (μV) | |
|---|---|---|---|
| | | GI87084B | Fentanyl |
| RIGHT HEMISPHERE (Occipital Frontal Leads) | | | |
| 0 | Control | 4.9 ± 0.9 | 8.1 ± 1.0 |
| 5 | ISO off | 7.4 ± 0.5 | 7.3 ± 1.3 |
| 10 | 0.3 | 7.8 ± 1.9 | 5.0 ± 0.6 |
| 20 | 1 | 6.3 ± 1.8 | 4.5 ± 0.5 |
| 30 | 3 | 5.6 ± 2.8 | 4.1 ± 0.5 |
| 40 | 10 | 4.8 ± 1.0 | 4.4 ± 0.4 |
| 50 | 30 | 6.0 ± 1.2 | 16.5 ± 2.9* |
| 60 | 100 | 4.3 ± 0.4 | NT |
| Seizure | | none | 25.3 ± 1.3* |
| 70 | PT-Z | 31.5 ± 8.0* | 34.4 ± 5.7* |
| LEFT HEMISPHERE (Occipital Frontal Leads) | | | |
| 0 | Control | 5.8 ± 0.1 | 7.6 ± 1.4 |
| 5 | ISO off | 8.5 ± 0.9 | 7.4 ± 1.0 |
| 10 | 0.3 | 5.7 ± 1.2 | 5.2 ± 0.6 |
| 20 | 1 | 5.6 ± 0.7 | 5.2 ± 0.4 |
| 30 | 3 | 5.4 ± 1.4 | 4.9 ± 1.0 |
| 40 | 10 | 6.0 ± 2.2 | 7.0 ± 2.2 |
| 50 | 30 | 7.0 ± 2.3 | 8.4 ± 1.9 |
| 60 | 100 | 6.3 ± 1.3 | NT |
| Seizure | | none | 26.7 ± 2.3* |
| 70 | PT-Z | 35.6 ± 8.0* | 31.8 ± 4.6* |

These data are the mean ± SEM for 4–5 dogs. GI87084B or fentanyl was infused from 0 to 50 or 60 min as noted in the table.
*Indicates differences from control (time 0, < 0.05);
NT indicates doses not tested;
'ISO off' indicates termination of isoflurane administration;
PTZ indicates administration of pentylenctetrazole.

In the present study, no seizure activity was observed in the remifentanil treatment group at cumulative doses up to 54 mg/kg. Four of five dogs in the fentanyl group showed seizure activity on the EEG during infusion of the highest dose. During this time period, the cumulative dose of fentanyl was being increased from 4.9 to 15 mg/kg. In this direct comparison under similar conditions, remifentanil showed much less convulsant potential than fentanyl. The characteristic high voltage, high frequency EEG pattern expected during seizure activity was also observed after dosing with pentyienetetrazole, a known convulsant, used as a positive control.

Hemodynamic Effects

The hemodynamic effects for remifentanil (denoted as GI87084) are set forth below in Table 2.

TABLE 2

HEMODYNAMIC EFFECTS OF GI87084B INFUSTION IN ANESTHETIZED DOGS

| TIME (min) | DOSE (μmole/kg) | Heart Rate (bpm) | Left Ventricular +dP/dt (mmHg/sec) | Diastolic Blood Pressure (mmHg) | Systolic Blood Pressure (mmHg) | LV End Diastolic Pressure (mmHg) | Cardiac Output (L/min) | Systemic Vascular Resistance (mmHg/L/min) | Rate Pressure Product (bpm × mmHg) |
|---|---|---|---|---|---|---|---|---|---|
| 0 | Control | 132 ± 13 | 3180 ± 471 | 69 ± 8 | 104 ± 6 | 8 ± 1 | 3.4 ± 0.4 | 24 ± 2 | 13854 ± 1896 |
| 5 | ISO off | 90 ± 9* | 2581 ± 511 | 77 ± 7 | 114 ± 6 | 10 ± 2 | 2.3 ± 0.2* | 42 ± 6* | 10350 ± 1335 |
| 10 | 0.3 | 73 ± 9* | 4473 ± 564+ | 104 ± 11+ | 160 ± 7* | 17 ± 3 | 2.4 ± 0.2* | 53 ± 7* | 11787 ± 1742+ |
| 20 | 1 | 69 ± 5* | 4244 ± 401 | 95 ± 5+ | 151 ± 4*+ | 16 ± 2 | 2.4 ± 0.2* | 48 ± 5* | 10382 ± 476+ |
| 30 | 3 | 86 ± 2*+ | 3646 ± 546 | 89 ± 7+ | 148 ± 6*+ | 13 ± 2 | 2.2 ± 0.1*+ | 49 ± 4* | 9743 ± 411+ |
| 40 | 10 | 62 ± 3*+ | 3683 ± 429 | 80 ± 7+ | 143 ± 5* | 20 ± 4 | 2.2 ± 0.1*+ | 46 ± 4*+ | 8879 ± 467*+ |
| 50 | 30 | 63 ± 5*+ | 3290 ± 399 | 33 ± 5 | 135 ± 5* | 19 ± 6 | 2.1 ± 0.1*+ | 46 ± 4*+ | 8513 ± 754*+ |
| 60 | 100 | 112 ± 13 | 2356 ± 202 | 85 ± 9 | 126 ± 8* | 14 ± 2 | 2.9 ± 0.2 | 36 ± 4 | 14291 ± 2229 |

These data are the mean ± SEM for 4 dogs. Doses shown are non-cumulative.
'ISO off' denotes termination of isoflurane administration.
*Indicates values different from time 0 ($p < 0.05$).
+Indicates values significantly different from the fentanyl treatment group ($p < 0.05$).

EXAMPLE 2

The EEG effects of remifentanil and alfentanil in healthy volunteers was evaluated via a pharmacokinetic and pharmacodynamic comparison. The objective of this study was to characterize the relationship between the pharmacokinetics and pharmacodynamics of remifentanil in normal volunteers using the continuously processed EEG. Anesthesia doses of opioid drugs lead to the formation of delta waves on the EEG; a surrogate for maximal opioid anesthetic effect. Results from the first 20 subjects indicates that continuous infusions of remifentanil at rates of 1–8 g/kg/min for 20 minutes lead to loss of consciousness within 1.5 to 3 minutes after initiation of the infusion. Maximal slowing of the EEG occurs in a similar time frame. Recovery was rapid and complete (2–20 minutes). Recovery from alfentanil was more variable and took significantly longer. The infusion rates of remifentanil were 10–80 fold higher than the analgesic rates (0.05–0.1 g/kg/min) in humans.

EXAMPLE 3

The pharmacokinetics of remifentanil in patients undergoing elective inpatient surgery were evaluated. This was a single center, dose-escalation, pharmacokinetic study in 24 patients undergoing elective general surgical procedures. The pharmacokinetics of remifentanil were determined after a 1-minute infusion (2, 5, 15, 30 g/kg) was administered following tracheal intubation; serial arterial blood samples were collected for 6 hours. Unlike other N-phenyl-N-(4-piperidinyl)amides, remifentanil's total clearance was independent of dose and was approximately 3 to 4-fold higher than normal hepatic blood flow, consistent with rapid metabolism by blood and tissue esterases. This study demonstrated that remifentanil's elimination profile was rapid even after doses that were 30-fold higher than the analgesic doses in humans. Using a 240 minute infusion simulation, the time required for a 50% reduction in the hypothetical effect site concentration of remifentanil (8.7 minutes) was considerably less than that for sufentanil (33.9 minutes), alfentanil (58.5 minutes) and fentanyl (262 minutes).

EXAMPLE 4

Dose-finding and comparative trial of remifentanil and alfentanil for anesthesia maintenance was performed. The protocol was designed to investigate the safety and efficacy of remifentanil in the induction and maintenance of anesthesia in patients undergoing elective in-patient surgery procedures. Patients were induced with remifentanil (1 g/kg/min) or alfentanil (40 g/kg) in combination with propofol and vecuronium. Thereafter, patients received nitrous oxide (2:1 in oxygen) with the remifentanil or alfentanil infusion. Initial remifentanil infusion rates were 0.05, 0.1, 0.3, 0.6, and 1 g/kg/min, whereas the alfentanil patients received up to 1 g/kg/min. The opioid infusion rate was held constant until after surgical incision. After surgical incision, rates were increased on the basis of response to surgical stimuli. Preliminary evaluation of the response to surgical incision in 50 patients indicates remifentanil's ED50 for effective anesthesia with a nitrous-narcotic technique is 0.4 g/kg/min. Patients in the pilot study received up to 2 g/kg/min for 6 hours. Recovery from anesthesia was rapid. Spontaneous breathing was attained within 8 minutes after discontinuation of remifentanil and nitrous oxide. Remifentanil's ED50 for anethesia by a nitrous-narcotic technique was approximately 4-fold higher than the ED50 for analgesia.

EXAMPLE 5

A study of the effects of a benzodiazepine premedication on the dose response of remifentanil during anesthesia with respect to induction, maintenance and recovery. The purpose of this study was to determine the effect of a benzodiazepine on the effectiveness of remifentanil for anesthesia induction and maintenance. A pilot study was completed in 35 patients to determine the doses of remifentanil that were being administered in the double-blind, randomized study. Patients in this pilot study received up to 10 g/kg bolus and a 1 g/kg/min infusion of remifentanil without a benzodiazepine. Results from the pilot study demonstrated that patients could be rendered unconscious with remifentanil alone at the highest dose regimen. The small oral dose of the benzodiazepine (temazepam) administered preoperatively did not lead to loss of consciousness. Initiation of remifentanil infusions at 0.05–1.0 g/kg/min lead to rapid loss of consciousness.

EXAMPLE 6

A comparative study of remifentanil and alfentanil for the management of intraoperative stress responses in a balanced anesthetic technique was performed. The purpose of this study was to determine the infusion rates of remifentanil and alfentanil required for the maintenance of adequate anesthesia in patients undergoing elective surgery. Remifentanil patients received an initial dose of 2 g/kg bolus injection plus a continuous infusion at a rate of 0.25 g/kg/min. The infusion rate was adjusted based on the patients response to surgical stress. Patients received a benzodiazepine (midazolam IV) preoperatively and anesthesia was induced with remifentanil or alfentanil in combination with thiopental. Anesthesia was maintained with 66% nitrous oxide and the opioid infusion.

Results from 75 patients indicated that remifentanil (at infusion rates of 0.25–0.5 g/kg/min) is effective in maintaining anesthesia. Recovery from anesthesia after procedures lasting up to 8 hours is rapid (3–10 minutes). Postoperatively, the remifentanil infusion was decreased to 0.05–0.2 g/kg/minute to provide analgesia without respiratory depression. The remifentenil dose for nitrous anesthesia was greater than the analgesic doses postoperatively.

EXAMPLE 7

Minimum alveolar concentration (MAC) reduction of isoflurane with remifentanil was evaluated. The purpose of this study was to determine remifentanil's ability to decrease the end-tidal isoflurane concentration necessary to anesthetize patients. Patients were induced with isoflurane and 7 different dose levels of remifentanil. After endotracheal intubation, the isoflurane concentration was decreased in a controlled fashion. Response to surgical incision was evaluated to determine the effectiveness of remifentanil in order to decrease the need for isoflurane. Results from the first 35 patients (out of a total of 192 patients to be treated) indicated that remifentanil decreased the minimum alveolar concentreation (MAC or ED50) MAC for isoflurane from 1.2% to 0.25% (a 75% reduction in the need for anesthetic).

We claim:

1. A method for providing anesthesia in a mammal comprising administering to such mammal a compound having the Formula (I):

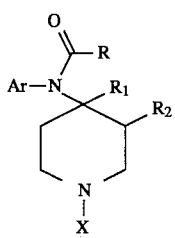

wherein X is a member selected from the group consisting of alkoxycarbonyl-lower alkyl, lower alkyl-carbonyloxy-lower alkyl, alkenyloxycarbonyl-lower alkyl, and $(C_{1-2})$alkoxy-$(C_{1-2})$alkoxycarbonyl-lower alkyl; Ar is a member selected from the group consisting of phenyl and mono-,di- and tri-substituted phenyl, wherein each substituent is independently selected from the group consisting of halo, lower alkyl, lower alkoxy and trifluoromethyl; R is a member selected from the group consisting of lower alkyl and lower alkoxy-lower alkyl; $R^1$ is a member selected from the group consisting of hydrogen and lower alkoxycarbonyl; and $R^2$ is a member selected from the group consisting of hydrogen and methyl; and the optically active and cis-trans isomers thereof and the acid addition salts thereof; said compound being administered to said mammal in an amount in excess of an amount effective for analgesia in order to induce or maintain anesthesia.

2. The method of claim 1, wherein said compound is administered parenterally.

3. The method of claim 1, wherein said compound is administered sublingually.

4. The method of claim 1, wherein said compound is administered transdermally.

5. The method of claim 1, wherein said compound is administered i.v. bolus.

6. The method of claim 5, wherein said compound is administered in an amount of about 8 to 20 g/kg.

7. The method of claim 6, wherein said compound is administered in an amount of about 0.1 to 3.0 g/kg/min.

8. The method of claim 1, wherein said compound is administered by continuous infusion.

9. The method of claim 1 wherein X is alkoxycarbonyl-lower alkyl.

10. The method of claim 1 wherein X is lower alkylcarbonyloxy-lower alkyl.

11. The method of claim 1 wherein X is alkenyloxycarbonyl-lower alkyl.

12. The method of claim 1 wherein X is alkoxycarbonyl-lower alkyl.

13. The method of claim 1 wherein Ar is phenyl or 2-fluorophenyl.

14. The method of claim 1 wherein R is ethyl.

15. The method of claim 1 wherein $R^1$ is methoxycarbonyl.

16. The method of claim 1 wherein said compound is selected from the group consisting of 5-[4-methoxycarbonyl-4-[(1-oxopropyl)phenylamino]-1-piperidine] pentanoic acid, methyl ester; 2-[4-methoxycarbonyl-4-[(1-oxopropyl)phenylamino]-1-piperidine]ethyl acetate; 3-[4-(1-oxopropyl)-2-fluorophenylamino]-1-piperidine]-propanoic acid, methyl ester; or 3-[4-methoxycarbonyl-4-[(oxopropyl)phenylamino]-1-piperidine] propanoic acid, vinyl ester and pharmaceutically acceptable acid addition salts thereof.

17. The method of claim 1 wherein said compound is 3-[4-methoxycarbony-4-[(1-oxopropyl)-phenylamino]-1-piperidine] propanoic acid, alkyl ester, and the pharmaceutically acceptable acid addition salts thereof.

18. The method of claim 1, wherein said mammal is a human.

19. The method of claim 18, wherein said compound of Formula (I) is administered in an amount at least 4 times in excess of its $ED_{50}$ for analgesia.

20. The method of claim 18, wherein said compound is administered in conjunction with a hypnotic in an effective amount to induce unconsciousness.

21. The method of claim 18, wherein said compound is administered in conjunction with a CNS depressant in an effective amount to induce unconsciousness.

22. The method of claim 18, wherein said compound is administered in an amount in excess of its $ED_{50}$ for analgesia.

23. The method of claim 22, wherein said compound is administered in conjunction with a hypnotic, an anxiolytic. or an inhaled agent being delivered in an amount less than 50% of its $ED_{50}$.

24. The method of claim 23, wherein said compound is administered in an effective amount to maintain anesthesia.

25. The method of claim 23, wherein said compound is administered alone or in conjunction with a hypnotic, an anxiolytic or an inhaled anesthetic agent in an amount such that upon discontinuing administration of said compound, said mammal recovers from anesthesia or sedation in less than 15 minutes.

26. The method of claim 25, wherein said hypnotic, anxiolytic and/or inhaled agent is administered in an amount such that upon discontinuing administration of said compound of Formula (I), said mammal recovers from anesthesia or sedation in less than 15 minutes.

27. A method for providing conscious sedation in a mammal comprising administering to such mammal a compound having the Formula (I):

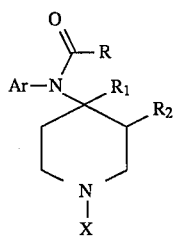

wherein X is a member selected from the group consisting of alkoxycarbonyl-lower alkyl, lower alkyl-carbonyloxy-lower alkyl, alkenyloxycarbonyl-lower alkyl, and $(C_{1-2})$alkoxy-$(C_{1-2})$alkoxycarbonyl-lower alkyl; Ar is a member selected from the group consisting of phenyl and mono-,di- and tri-substituted phenyl, wherein each substituent is independently selected from the group consisting of halo, lower alkyl, lower alkoxy and trifluoromethyl; R is a member selected from the group consisting of lower alkyl and lower alkoxy-lower alkyl; $R^1$ is a member selected from the group consisting of hydrogen and lower alkoxycarbonyl; and $R^2$ is a member selected from the group consisting of hydrogen and methyl; and the optically active and cis-trans isomers thereof and the acid addition salts thereof; said compound being administered to said mammal in an amount in excess of an amount effective for analgesia in order to induce or maintain conscious sedation.

* * * * *